United States Patent [19]

Korgemets

[11] 4,018,226
[45] Apr. 19, 1977

[54] ADULT UNDERGARMENT
[76] Inventor: Dorothy Korgemets, 9333 E. Jefferson, Detroit, Mich. 48214
[22] Filed: Sept. 2, 1975
[21] Appl. No.: 609,792

Related U.S. Application Data

[62] Division of Ser. No. 400,550, Sept. 25, 1973, Pat. No. 3,916,901.
[52] U.S. Cl. .............................................. 128/287
[51] Int. Cl.$^2$ ......................................... A61F 13/16
[58] Field of Search .................. 128/287, 286, 284

[56] References Cited

UNITED STATES PATENTS

| | | | |
|---|---|---|---|
| 2,599,355 | 6/1952 | Stepp | 128/287 |
| 2,606,558 | 8/1952 | Kennette | 128/287 |
| 2,695,615 | 11/1954 | DelGuercio | 128/287 |
| 2,698,620 | 1/1955 | Larkins | 128/287 |
| 2,921,583 | 1/1960 | Lerner | 128/287 |
| 2,967,526 | 1/1961 | Olson | 128/287 |
| 3,039,466 | 6/1962 | Wilson | 128/287 |
| 3,049,124 | 8/1962 | Thompson | 128/287 |
| 3,494,361 | 2/1970 | Thivat | 128/287 |

Primary Examiner—John D. Yasko
Attorney, Agent, or Firm—Basile, Weintraub and Vanophem

[57] ABSTRACT

An adult undegarment fabricated from a cloth material formed into front and back panels connected by a narrow central panel forming a crotch portion. The front and back panels are provided with tie cords for facilitating the attachment of the garment to the waist of a patient. The crotch portion of the garment is so sized as to provide on opposite sides thereof, leg portions to receive the legs of the patient when the panels are attached to the patient. The crotch portion includes tie cords for securing the lower portion of the garment around the patient's legs. The garment is adapted to have various cloth and water impervious panels attached thereto such that the garment may be modified for a wide variety of uses.

4 Claims, 8 Drawing Figures

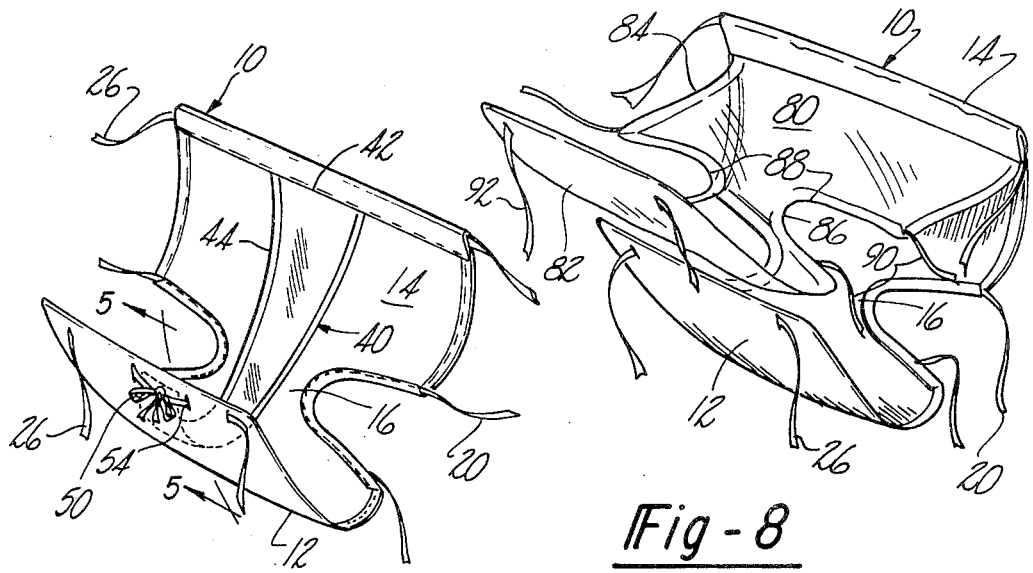
Fig-4
Fig-8
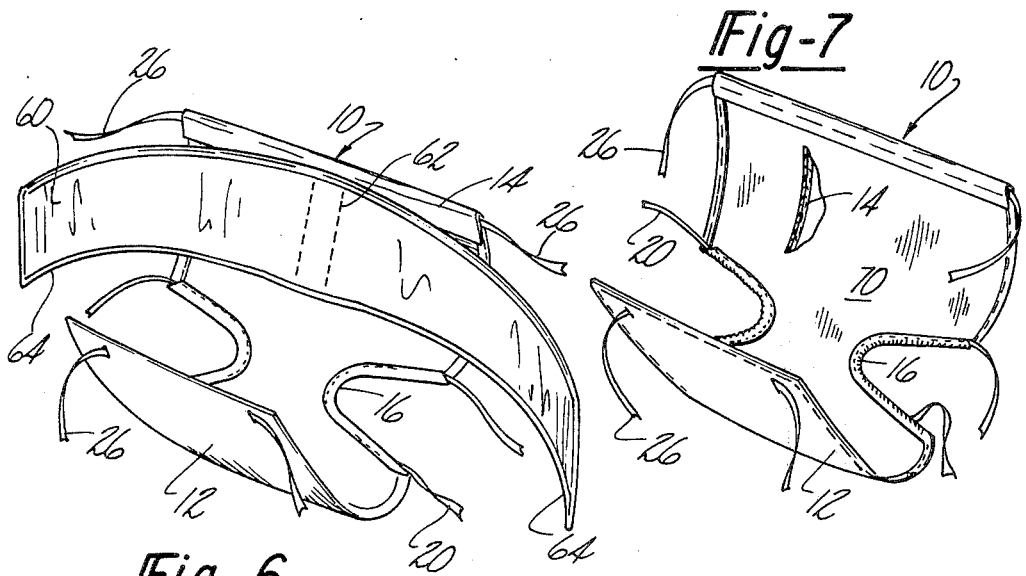
Fig-7
Fig-6
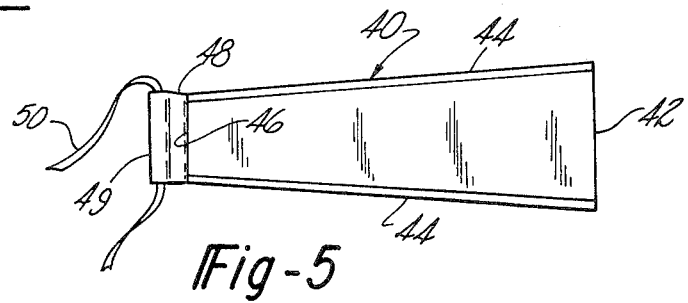
Fig-5

ADULT UNDERGARMENT

This is a division of application Ser. No. 400,550, filed Sept. 25, 1973 now U.S Pat. No. 3,916,901.

BACKGROUND OF THE INVENTION

I. Field of the Invention

The present invention relates to an adult undergarment particularly designed for both male and female patients for hospital or nursing home use.

II. Description of the Prior Art

Heretofore numerous diapers and undergarments have been devised for use in conjunction with hospitalized persons and, particularly, the aged and invalid persons who are bedridden. In addition, similar garments have been devised for use with infants and are normally referred to as baby diapers. Both types of garments are disclosed in numerous patents such as U.S. Pat. Nos. 2,599,355, 3,483,864, 3,653,381, 3,554,195, 3,150,664, 2,466,184, 2,583,553, 2,767,714, 3,349,769 and 2,025,843. All of these patents are directed to various means for providing a moisture proof protective covering for disposable and similar pads and washable or disposable diapers. Although these garments may function in an acceptable manner to achieve the desired results of providing a moisture proof protective covering, it is envisioned that the garment fabricated in accordance with the principles of the present invention will have a wide variety of uses including the support of a disposable diaper.

SUMMARY OF THE INVENTION

The present invention which will be described subsequently in greater detail comprises a cloth garment having front and rear panels connected by means of a narrow section to permit the garment to be placed about the body of a patient in such a manner that the crotch and lower abdominal regions are covered. The cloth garment includes means for releasably fastening the garment to the wearer. Modifications of the basic garment include a moisture proof protective covering for the support of disposable pads, anal and abdominal dressing pads. Each of the modified garments includes means for providing support for drainage tubes that may be attached to the wearer's body.

It is therefore a primary object of the present invention to provide an adult undergarment which may preferably be worn by patients of a hospital or nursing home so as to avoid embarrassment of the patient who, when wearing normal hospital garments, may have portions of their body exposed.

It is also an object of the present invention to provide a garment having an economical moisture proof covering for the support of a water absorbent or moisture absorbent material.

It is still an object of the present invention to provide an adult undergarment which is easily adjustable in size, yet one which is so shaped as to provide a snug and comfortable fit.

It is still an object of the present invention to provide a one piece garment specifically designed for hospital or nursing home use and adapted to be worn either by male or female patients.

It is yet another object of the present invention to provide a one piece undergarment which with minor modifications may be employed as a geriatric incontinent dressing support having a full moisture resistant inner lining and usable with a disposable diaper.

It is still a further object of the present invention wherein the basic one piece undergarment may be utilized with minor modification as a binder for securing dressings in place.

Other objects, advantages and applications of the present invention will become apparent to those skilled in the art when the following description of several examples of the best modes contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and in which:

FIG. 4 is a perspective view of a second example of the present invention wherein the garment is used as a perineum anal dressing support;

FIG. 5 is a plan view of a portion of the garment illustrated in FIG. 4;

FIG. 6 is a perspective view of yet another modification of the inventive garment wherein the garment utilizes an abdominal back dressing support;

FIG. 7 is still another modification of the present invention wherein the inventive garment is shown as a geriatric incontinent dressing support; and FIG. 8 is a perspective view of the inventive garment shown as a geriatric incontinent dressing support.

DESCRIPTION OF THE PREFERRED EMBODIMENTS

Figure 1:
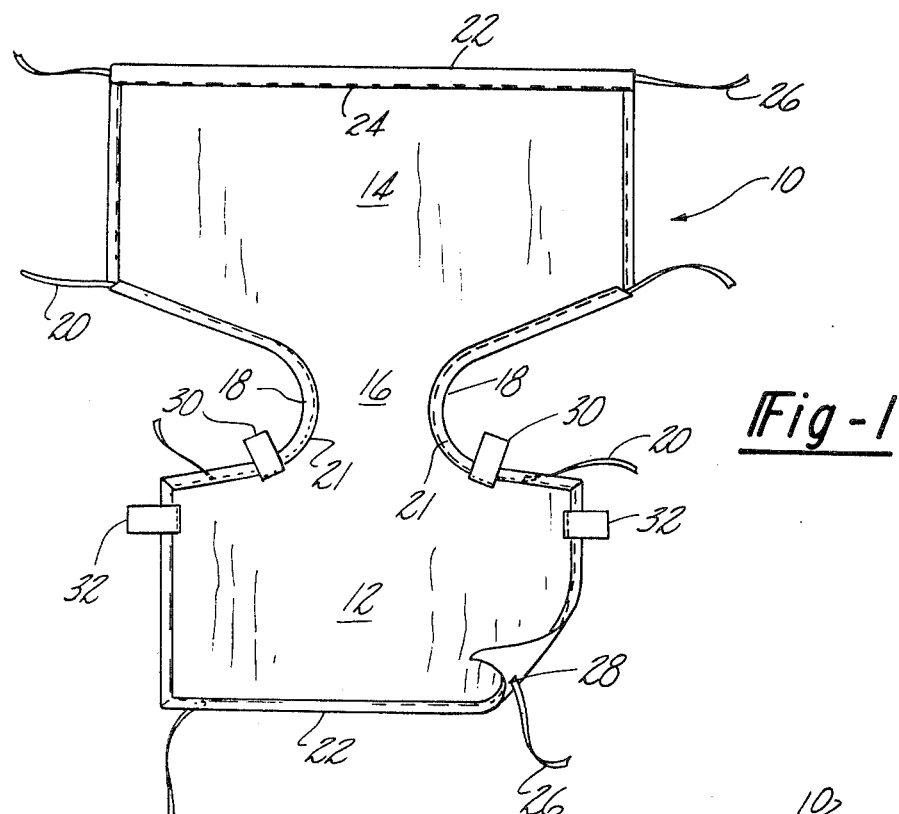
FIG. 1 is a plan view of an adult undergarment which has been manufactured in accordance with the principles of the present invention and is shown in a laid-out flat view.
Figure 3:
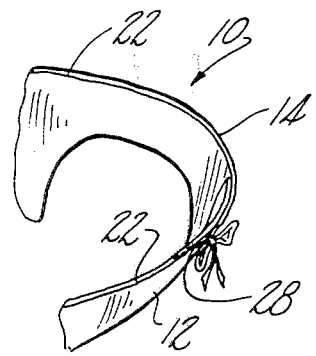
FIG. 3 is a fragmentary perspective view of the adult garment illustrated in FIGS. 1 and 2 with the upper tie cords being attached for illustrating the overlapping features of the garment panels.
Figure 2:
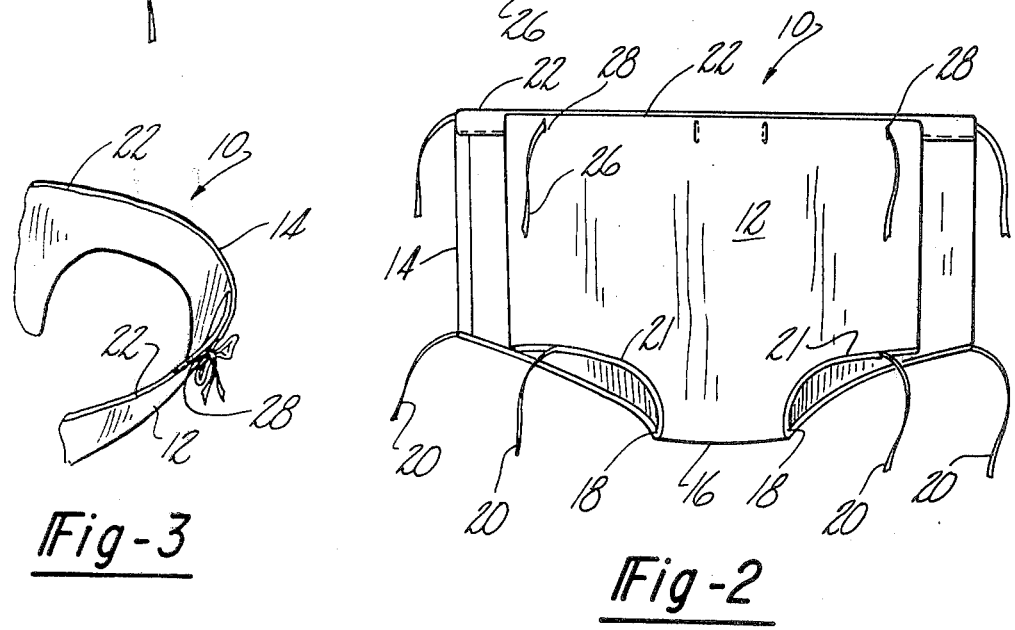
FIG. 2 is a front elevational view of the adult diaper illustrated in FIG. 1 with the diaper being shown in a partially assembled upright position.

Referring now to the drawings and, in particular, to FIGS. 1, 2 and 3 where there is shown one example of an adult garment 10 comprising a cloth material having a front panel section 12 and a rear panel section 14 connected by a narrowed center section 16 which forms the crotch portion of the adult garment 10. The center portion 16 has concave marginal edges 18 which are adapted to fit between the legs of the person wearing the garment while the concave edges have divergent ends that wrap around the legs and which are connected to each other by means of tie cords 20. The material along the center portion 16 and along the lower edges of the front and rear panels are turned inwardly to form loops which slidably receive the tie cords 20 so that the material may be drawn in as the tie cords 20 are tightened, whereby the garment may fit a wide range of leg sizes.

Similarly, the upper edges 22 of the front and rear panels are turned over and sewn to the front and rear panels to form loops 24 which slidably receive tie cords 26. As can best be seen in FIGS. 1 and 2, the sewn portion along the upper edge 22 of the front panel 12 terminates at a point 28 inwardly spaced from the outer side edges of the front panel 12 such that the ends of the tie cord 26 exit the material at this inwardly spaced point for a purpose to be described hereinafter. The front and rear panels 12 and 14 respectively are generally rectangular in shape except for their lower edges which are curved to form the center crotch portion 16, as hereinbefore described. As can best be seen in FIG. 2 the front panel 12 has a smaller width than the back panel 14 such that when the garment 10 is worn by an individual the side edges of the back panel 14 will wrap around the side of the individual for attachment to the front panel 12 by means of the tie cords 20 and 26. In this position the inner surface of the side edges of the back panel 14 are overlapping the front surface of the front panel 12 along the side thereof in the manner illustrated in FIG. 3. This overlapping of the side edges of the front and back panels provides a dual purpose. Firstly, the overlapping conceals the person's body and eliminates the aforementioned embarrassment associated with the standard hospital gowns so that a person can be afforded relative privacy which is totally lacking in such conventional hospital gowns. Secondly, the overlapping of the front and back panel and the provision of a larger back panel coming around to the front of the individual results in the tie cord knots being accurately spaced from the side of a patient such that when the patient is resting on his side he will not be resting on the knots, and any discomfort which would result from lying on the knots is completely eliminated.

As can best be seen in FIG. 1, the front panel 12 is provided with tabs 30 along its lower edge immediately adjacent the crotch portion 16, while tabs 32 are provided along the side edges of the front panel 12. The tabs 30 and 32 function to provide a means for attaching drainage tubes that may be connected to the person wearing the garment. Heretofore, it has been necessary to tape such tubes to the person and such taping has resulted in a general discomfort all of which is eliminated by the provision of the tabs 30 and 32 to the garment 10.

Referring now to FIGS. 4 and 5 wherein there is illustrated a modification of the present invention in the form of the garment 10 with a perineum anal dressing support band 40 attached thereto. The band, which can best be seen in FIG. 5, is trapezoidal in shape with the base end 42 being sewn to the upper edge of the back panel 14. The trapezoidal section of the band 40 is preferably fabricated from a plastic material with the lengthwise edges 44 thereof having an elastic material sewn thereon. The upper edge 46 of the band 40 has a fabric 48 such as cotton sewn thereon. The cotton fabric 48 has a loop 49 sewn thereon and through which a tie cord 50 is disposed. As can best be seen in FIG. 4, the tie cord 50 extends through loops 54 formed in the mid-section of the front panel 12 to permit the securing of the band 40 to the front panel 12. The band 40, as aforementioned, is preferably fabricated from a moisture resistant material, such as rubber or plastic, and because of the aforementioned manner of attaching the band 40 to the front panel 12 of the garment, the dressing band 40 is adjustable in size and will easily hold dressings in place irrespective of the size of the person on which the garment 10 is being utilized.

Referring now to FIG. 6 wherein there is illustrated another embodiment of the present invention in the form of the garment 10 having abdominal binder 60 attached thereto. The binder 60 which is sewn to the mid-section 62 of the back panel 14 is preferably made of a cotton material or the like and has an elastic material 64 sewn to its peripheral edges. The binder 60 is used to support dressing in a proper position around the abdominal portions of the patient's body. The elastic material 64 in the edges of the binder 60 provides an adjustable feature which is desirable in such a binder. The garment 10 is then secured to the patient in the aforementioned manner.

Referring now to FIG. 7 wherein there is illustrated another embodiment of the present invention in the form of the basic garment 10 having a moisture resistant lining 70 fabricated from a rubber or plastic material. The lining 70 has a contour which is complementary in shape to the shape of the garment 10 and is sewn thereto along its peripheral edges. The garment 10 with the lining 70 may be utilized as a geriatric incontinent dressing and used with a disposable diaper or the like.

Referring now to FIG. 8 for an improved version of the garment illustrated in FIG. 7. The FIG. 8 embodiment comprises the basic garment 10 and a plastic material 80 having a shape complementary to the shape of the garment 10 including a front panel 82 and a back panel 84 connected by a center section 86. The concave edge of the center section and lower edges of the front and back panels have an eleastic material 88 sewn thereon and provides a means for securing tie cords 90 to the leg portions. The upper edge of the back panel of the plastic material 80 is sewn to the upper edge of the back panel 14 of the standard garment 10, while the front edge of the front panel has tie cords 92 attached thereto in the same manner as the front panel 12 of the basic garment 10. In use, a suitable diaper may be attached or carried between the legs of the patient wearing the garment 10 with the plastic portion 80 tied to the body followed by attachement of the basic garment 10 to the body by means of the tie cords 20 and 26 in the same manner as originally described with respect to the basic garment 10. The utilization of the basic garment with the semi-attached plastic garment 80 as shown in FIG. 8 provides numerous advantages over the embodiment disclosed in FIG. 7. Particularly, as a person is sleeping during the night, his movement relative to the bed may cause sliding of the basic garment 10 with respect to the bed, whereas the plastic garment 80 will stay relatively stationary on the patient's body preventing the leakage of any fluid from the diaper contained therein.

It can thus be seen that one basic garment specifically designed for patients in hospitals or nursing homes has been disclosed; it is one which is practical for use on both male and female patients, in that, it is adjustable to accommodate varying sized patients; it is one which with minor modifications may be utilized for geriatric incontinent dressings, perineum anal dressings or abdominal back dressings.

Although several embodiments of the present invention have been disclosed, it should be understood by those skilled in the art of undergarments that other forms may be had, all coming within the spirit of the invention and scope of the appended claims.

What is claimed is as follows:

1. An adult undergarment comprising a cloth material having a back panel and a front panel, each having inside and outside surfaces, connected by a narrow central panel defined by opposed inwardly curved sides constituting crotch portions and convergent end sections disposed along the lower edges of said panels and constituting pant leg portions;

channels extending along the length of the crotch portions, the convergent end sections and along the width of said front and back panels at the outer edges thereof, the channels of the leg portions and the outer edge of the front panel opening to said outside surface of said front panel at locations which are inwardly spaced from the side edges of said front panel, the channels of the leg portions and of the outer edges of the rear panel opening to the side edges of said rear panel, said entire front panel from side edge to side edge being smaller than said back panel; and tie cords movably carried within each of said channels, the ends of said tie cords existing from said openings, whereby portions of said back panel overlap portions of said front panel when said garment is worn and the ends of said tie cords are fastened together.

2. The adult undergarment defined in claim 1 further comprising tab means connected to said front panel along a portion of the divergent end section, said tab means being of sufficient strength and size to mount a drainage tube attachment.

3. The adult undergarment defined in claim 1 further comprising tab means attached along the side edge of said front panel, said tab means being of sufficient strength and size to mount a drainage tube attachment thereto.

4. The adult undergarment defined in claim 1 further comprising a water impervious material having a shape complementary to the shape of said cloth material and means fastening the outer edges of said cloth portion to said water impervious material.

* * * * *

UNITED STATES PATENT AND TRADEMARK OFFICE
CERTIFICATE OF CORRECTION

PATENT NO. : 4,018,226
DATED : April 19, 1977
INVENTOR(S) : Dorothy Korgemets

It is certified that error appears in the above-identified patent and that said Letters Patent are hereby corrected as shown below:

Page 1, [57], line 6, after "adult" delete "undegarment" and insert --undergarment--;

Column 3, line 26, preceding "spaced" delete "accurately" and insert --arcuately--;

Column 4, line 26, preceding "material" delete "eleastic" and insert --elastic--;

Column 4, line 36, after "by" delete "attachement" and insert --attachment--.

Signed and Sealed this nineteenth Day of July 1977

[SEAL]

Attest:

RUTH C. MASON
Attesting Officer

C. MARSHALL DANN
Commissioner of Patents and Trademarks